(12) United States Patent
Saito et al.

(10) Patent No.: US 7,775,664 B2
(45) Date of Patent: Aug. 17, 2010

(54) INSTRUMENT FOR MEASURING A REFRACTIVE POWER

(75) Inventors: Nobuo Saito, Tokyo (JP); Yasuhide Takahashi, Tokyo (JP); Kenichi Takahashi, Tokyo (JP); Yuuichi Kimura, Tokyo (JP)

(73) Assignee: Right Mfg. Co., Ltd., Tokyo (JP)

( * ) Notice: Subject to any disclaimer, the term of this patent is extended or adjusted under 35 U.S.C. 154(b) by 0 days.

(21) Appl. No.: 12/157,423

(22) Filed: Jun. 10, 2008

(65) Prior Publication Data

US 2008/0309877 A1   Dec. 18, 2008

(30) Foreign Application Priority Data

Jun. 12, 2007   (JP) ............... 2007-155225

(51) Int. Cl.
*A61B 3/10* (2006.01)
(52) U.S. Cl. ............... 351/221; 351/206; 351/208
(58) Field of Classification Search .......... 351/221
See application file for complete search history.

(56) References Cited

U.S. PATENT DOCUMENTS

| | | | |
|---|---|---|---|
| 4,390,255 A * | 6/1983 | Nohda et al. | ............. 351/212 |
| 5,561,482 A | 10/1996 | Miyake | |
| 5,629,747 A | 5/1997 | Miyake | |
| 5,909,268 A * | 6/1999 | Isogai et al. | ............. 351/208 |
| 6,152,565 A * | 11/2000 | Liu et al. | ............. 351/212 |
| 7,128,417 B2 * | 10/2006 | Isogai | ............. 351/206 |
| 7,154,111 B2 * | 12/2006 | Shaver | ............. 250/559.16 |
| 7,517,083 B2 * | 4/2009 | Blum et al. | ............. 351/168 |
| 2005/0110951 A1 * | 5/2005 | Yancey et al. | ............. 351/221 |

FOREIGN PATENT DOCUMENTS

| | | |
|---|---|---|
| JP | 4-009133 | 1/1992 |
| JP | 7-213485 | 8/1995 |
| JP | 8-164114 | 6/1996 |

* cited by examiner

*Primary Examiner*—Jessica T Stultz
(74) *Attorney, Agent, or Firm*—Dilworth & Barrese LLP

(57) ABSTRACT

An instrument for measuring a refractive power including an astigmatic axis with retinoscopy is provided, which includes a projector, a light receiving device, a detector, and a notification unit. The projector projects light into a pupil of an examined eye. The light receiving device receives light reflected from the examined eye. The detector detects a tilt angle of the light receiving device with respect to a measurement reference. The notification unit conveys information related to a result of detection performed by the detector.

14 Claims, 5 Drawing Sheets

INSTRUMENT FOR MEASURING A REFRACTIVE POWER

This application is based on and claims the benefit of priority from Japanese Patent Application No. 2007-155225, filed on 12 Jun. 2007, the content of which is incorporated herein by reference.

BACKGROUND OF THE INVENTION

1. Field of the Invention

The present invention relates to an instrument for measuring a refractive power of an examined eye.

2. Related Art

An instrument for measuring an eye refractive power has been widely used in medical facilities such as an ophthalmological clinic. Examples for such an instrument employ retinoscopy, which are described in Japanese Unexamined Patent Application Publication No. H7-213485 and No. H8-164114.

However, these examples have drawbacks related to a decrease in reliability of data measured for an astigmatic axis (axial angle of astigmatism), which may occur when the instrument is placed with a rotational bias relative to an examined eye. Particularly, when an instrument of a handheld type is used, the reliability of an astigmatic axis tends to be degraded due to handshaking of an operator.

SUMMARY OF THE INVENTION

The present invention provides an instrument for measuring a refractive power that can obtain measured data with higher reliability.

In an aspect of the present invention, an instrument for measuring a refractive power including an astigmatic axis with retinoscopy is provided, which includes a projector, a light receiving device, a detector, and a notification unit. The projector projects light into a pupil of an examined eye. The light receiving device receives light reflected from the examined eye. The detector detects a tilt angle of the light receiving device with respect to a measurement reference. The notification unit conveys information related to a result of detection performed by the detector.

The instrument described above that notifies an operator of the tilt angle detected with respect to the measurement reference allows the operator to adjust the tilt angle of the instrument according to the notification. In this way, the instrument according to the invention can increase the reliability of the measured data, particularly for an astigmatic axis.

In another aspect of the present invention, an instrument for measuring a refractive power is provided, in which the measurement reference is a reference line extending in one of horizontal and vertical directions.

With the instrument described above that has the reference line extending in one of the horizontal vertical directions, it is possible to increase the reliability of the measurement data for a normal measurement where an examinee in an upright position orients his eyes in a horizontal direction.

In still another aspect of the present invention, an instrument for measuring a refractive power is provided, in which the measurement reference is a reference line that connects substantially central points of left and right eyes of an examinee.

When the reference line has a tilt with respect to the horizontal direction: the face of the examinee has a tilt in left and right directions; or the examinee lies, for example, the instrument described above can adjust the tilt angle so as to be in agreement with the tilt of reference line. This allows the measurement data to have high reliability.

In yet another aspect of the present invention, an instrument for measuring a refractive power is provided, in which the notification unit includes a display device that displays the information related to the result of detection performed by the detector.

With the instrument described above, an operator can correct the tilt angle according to the displayed information.

In a further aspect of the present invention, an instrument for measuring a refractive power is provided, which further includes a refractive power measuring portion that compensates data related to the measured astigmatic axis in accordance with the result of detection performed by the detector.

The instrument described above can obtain the measurement data with high reliability even if the measurement is performed with the tilt angle.

In a still further aspect of the present invention, an instrument for measuring a refractive power is provided, in which the instrument is of a handheld type to allow an operator to perform measurement while holding the instrument.

Since the instrument described above does not have restriction on the posture of an examinee during measurement, deferring from an instrument of a desktop type, it allows measurement with high reliability for examinees in various situations.

DETAILED DESCRIPTION OF THE INVENTION

Exemplary embodiments of the present invention are hereinafter described in detail with reference to the attached drawings.

A coordinate system that is defined in the following manner is hereafter applied to descriptions: a first axis is called an X-axis, a second axis perpendicular to the X-axis is called a Y-axis that defines a horizontal plane with the X-axis, and a third axis perpendicular to the horizontal plane is called a Z-axis.

Utilizing retinoscopy, an instrument 51 for measuring a refractive power measures a refractive power of an examined eye, which includes a spherical power, astigmatic power and astigmatic axis.

Figure 1:
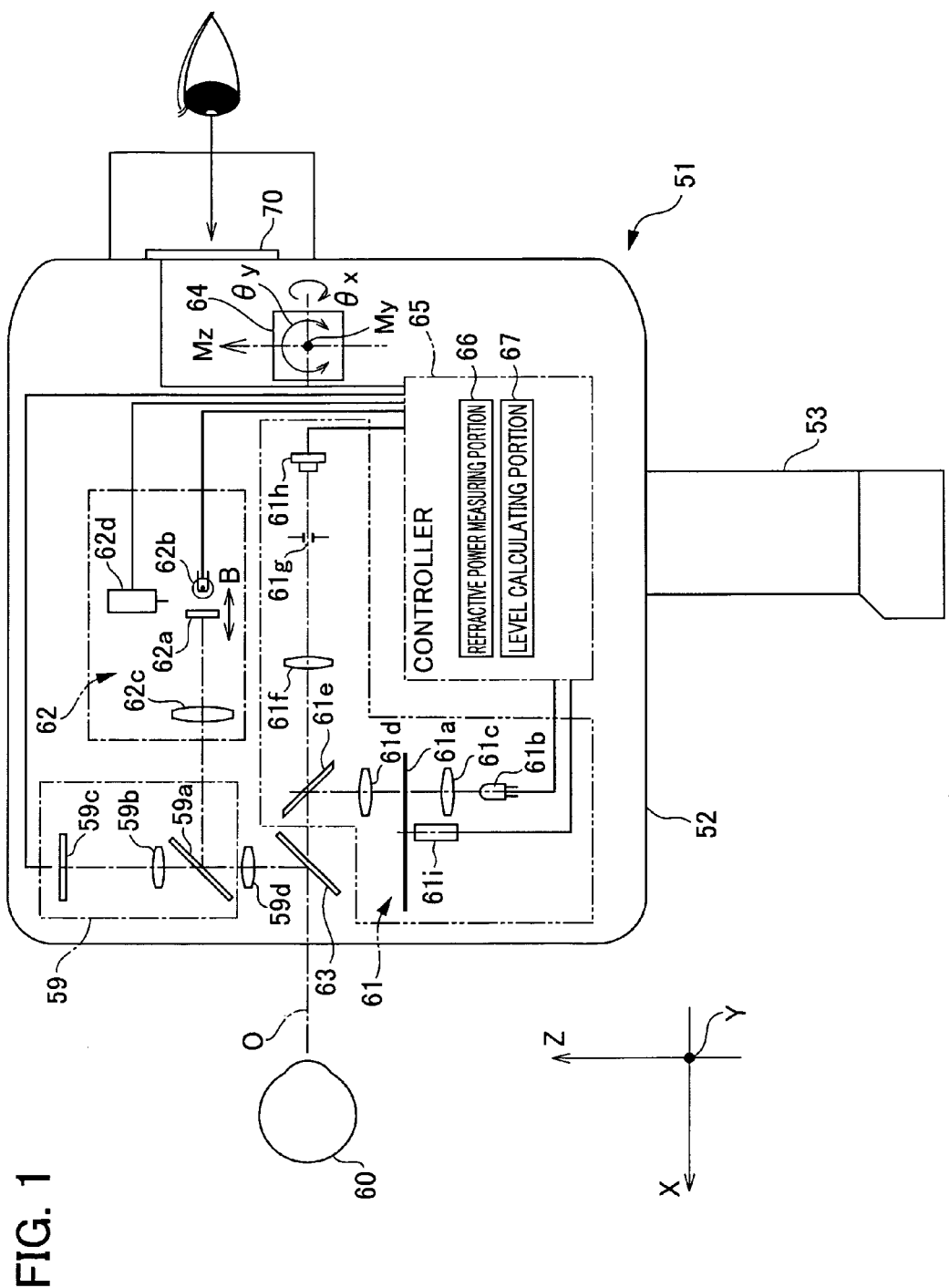
FIG. 1 is a schematic diagram illustrating the architecture of an instrument for measuring a refractive power according to an exemplary embodiment of the present invention.

As shown in FIG. 1, the instrument 51 is of a handheld type with a grip 53, which is held by an operator while a measurement is performed. The operator orients the instrument 51 such that an optical axis O is parallel with the X-axis, and introduces light for measurement into an examined eye 60.

The instrument 51 includes a case 52, grip 53, image capturing unit 59, measurement unit 61, projector 62, dichroic mirror 63, horizontal sensor 64 (tilt angle detector), controller 65, and monitor 70.

The grip 53 is secured to the case 52 such that a longitudinal direction of the grip 53 is aligned with a vertical direction so as an operator to comfortably hold during a measurement.

The image capturing unit 59 captures an image of the examined eye 60 and transmits the information related to the image to the controller 65. The image capturing unit 59 has a half mirror 59a, convex lens 59b, charge coupled device (CCD) 59c, and convex lens 59d. Near infrared light coming from the examined eye 60, which is reflected off the dichroic mirror 63, penetrates the half mirror 59a, being guided to an image capturing surface of the CCD 59c. Since the near infrared light passes through the convex lenses 59d and 59b, it focuses on the image capturing surface of the CCD 59c. In this way, the image capturing unit 59 can acquire the information related to the image of the examined eye 60.

The projector 62 has a convex lens 62c, target 62a, and visible light source 62b, which lie in this order closer to the examined eye 60. The projector further has a motor 62d.

Rays of light coming from the target 62a that are illuminated by the visible light source 62b focuses on a retina of the examined eye 60 after undergoing the following sequence: passing through the convex lens 62c; reflecting off the half mirror 59a; passing through the convex lens 59d; reflecting off the dichroic mirror 63; and entering the examined eye 60. In this connection, the rays of light coming from the target 62a are transformed into substantially parallel rays of light as a result of passing through the convex lenses 62c and 59d, entering the examined eye 60. In this way, the examined eye 60 sees the target 62a as if it lies more distant than it actually does.

In the projector 62, the motor 62d allows the target 62a and the visible light source 62b to be movable along an optical axis (in a direction shown by an arrow B in FIG. 1) via a target moving mechanism (not shown). While the target 62a and the visible light source 62b move along the optical axis of the examined eye 60, the relative position between these two components is maintained constant.

A measurement unit 61, which employs retinoscopy as measurement theory, measures a refractive power by detecting a phase difference in a movement of shade on a retina.

The measurement unit 61 includes means for projecting a pattern (a projector for projecting light for measurement), which includes a chopper 61a with slits, motor 61i for rotationally driving the chopper 61a, infrared light source 61b for illuminating the chopper 61a, lens 61c, and lens 61d projecting the pattern generated by the chopper 61a onto an eyeground of a pupil of the examined eye 60. The measurement unit 61 also has a light receiving device 61h that detects a velocity of movement of the pattern formed by returning light reflected off the eyeground of the examined eye 60, half mirror 61e, lens 61f, and apperture diaphragm 61g.

The light for measurement (infrared light) emitted from the measurement unit 61 is introduced into the examined eye 60 by the half mirror 61e. In contrast, the light for measurement (visible light) is introduced into the examined eye 60 by the half mirror 59a and the dichroic mirror 63. Since the chopper 61a of the measurement unit 61 rotates, the pattern projected on the eyeground of the examined eye 60 moves. Accordingly, the infrared light returning from the examined eye 60 results in a variation of the velocity of movement of the pattern formed on the light receiving device 61h according to the refractive power of the examined eye 60.

Figure 2:
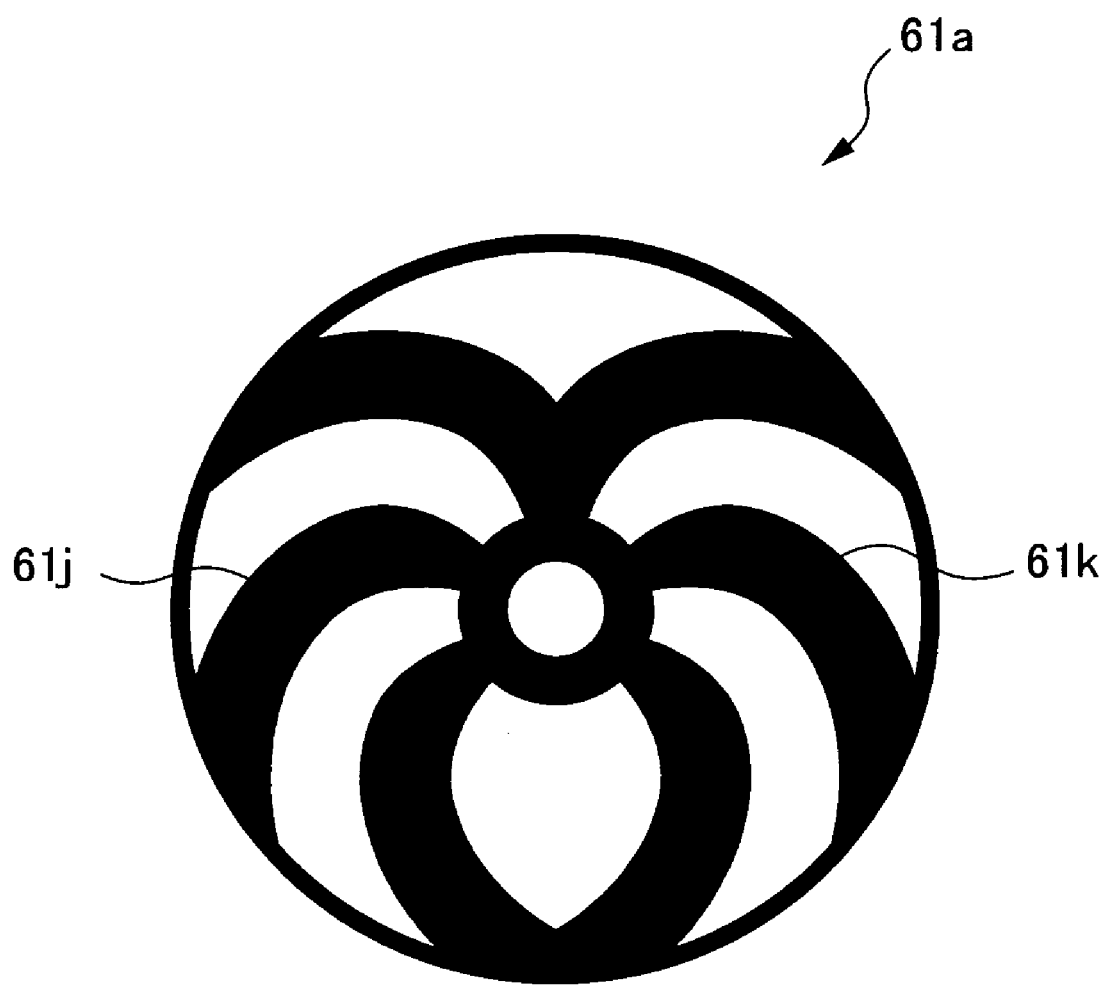
FIG. 2 is a diagram illustrating a pattern of a chopper according to the exemplary embodiment.

As shown in FIG. 2, the chopper 61a has two types of patterns 61j and 61k, whose images are reflected off the pupil of the examined eye 60 to focus on the light receiving device 61h when the chopper 61a completes one rotation.

The light receiving device 61h employs an image capturing device that is capable of capturing an image of light reflected off the pupil of the examined eye 60.

Figure 3:
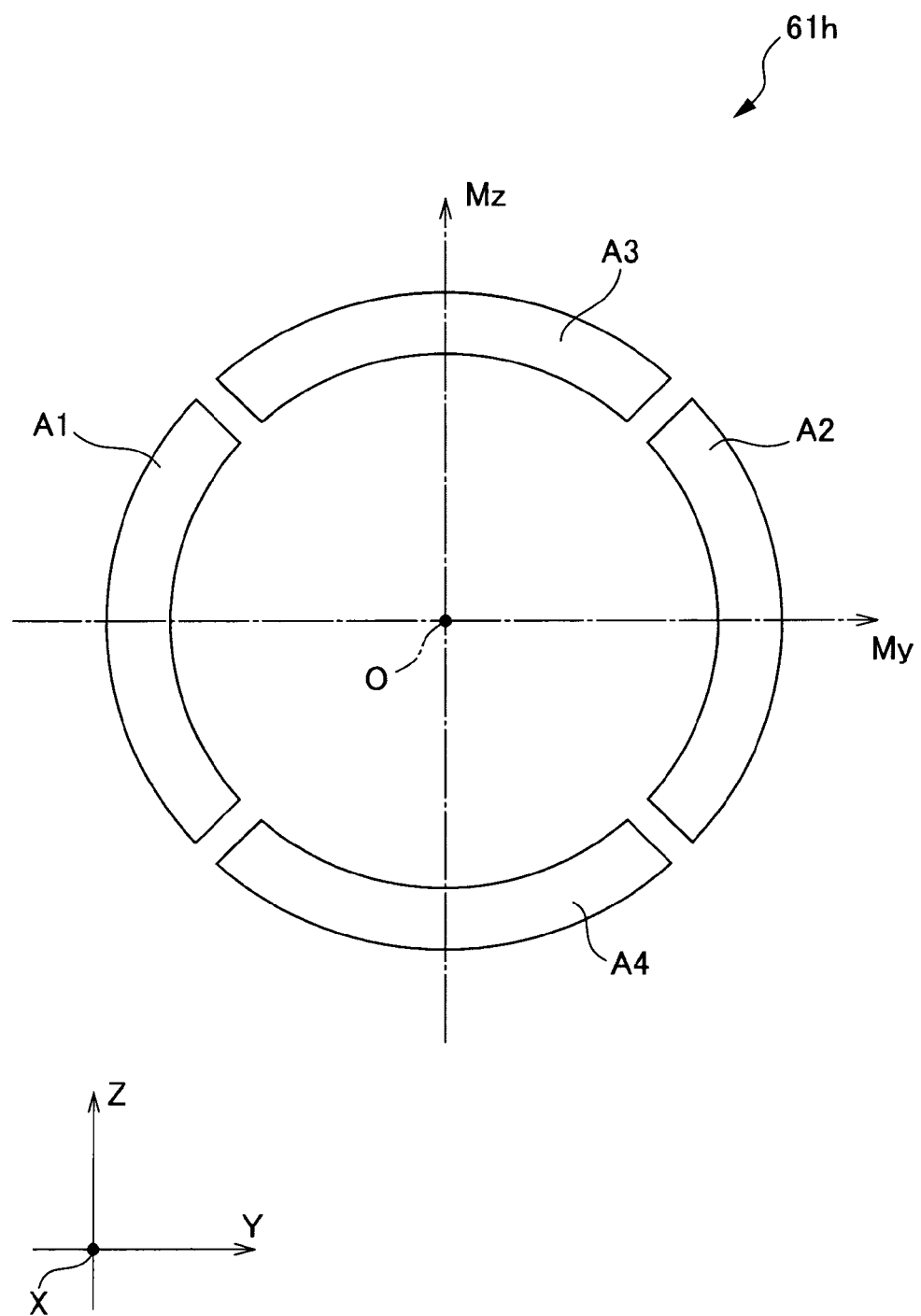
FIG. 3 is a diagram illustrating a light receiving area according to the exemplary embodiment.

As shown in FIG. 3, the light receiving device 61h is configured to have light receiving areas A1 and A2 shaped like arced sections, which are disposed to be opposite to each other in a direction of an axis $M_y$ that corresponds to a direction to scan the pattern for the examined eye 60. Similarly, light receiving areas A3 and A4 are disposed in a direction of an axis $M_z$ to scan the pattern for the examined eye 60, which is perpendicular to the axis $M_y$. It should be noted that a direction perpendicular to the axes $M_y$ and $M_z$ corresponds to an optical axis O. The light receiving unit 61 measures a phase difference between a pair of the light receiving areas (a pair of A1 and A2 and a pair of A3 and A4) so as to output a direction of movement and a size of the optical pattern, thereby allowing for a calculation of a refractive power such as a spherical power, astigmatic power and astigmatic axis. In the present embodiment, the instrument 51 for measuring a refractive power can perform one measurement with one rotation of the motor 61i (one rotation of the chopper 61a).

As described later, it is necessary to place the instrument 51 for measuring a refractive power such that the direction of the scanning axis $M_y$ is parallel with the Y-axis (a reference line) in a horizontal direction in order to obtain refractive power data having high reliability.

The dichroic mirror 63 allows the infrared light coming from the examined eye 60 to pass through to return to the measurement unit 61. On the other hand, the dichroic mirror 63 reflects the visible light coming from the examined eye 60 to guide it toward the CCD 59c.

As shown in FIG. 1, the horizontal sensor 64 is an acceleration sensor detecting the gravity acting on it. The horizontal sensor 64 is of a two-axis type that can detect tilt angles of the light receiving device 61h about the X-axis (see an arrow $\theta_x$) and the Y-axis (see an arrow $\theta_y$). The horizontal sensor 64 outputs detected signals to the controller 65. The horizontal sensor 64 is configured such that one of the two axes is aligned with the axis $M_y$ in a scanning direction (see FIG. 4). In this way, if the axis $M_y$ is parallel with the Y-axis, the horizontal sensor 64 outputs a tilt angle "zero" of the light receiving device 61h about the X-axis perpendicular to the Y-axis.

In addition, the horizontal sensor 64, in which the other axis direction for detecting acceleration is aligned with the optical axis O (see FIG. 1) of light for measurement received by the light receiving device 61h, can detect a tilt angle of the light receiving device 61h about the Y-axis.

The controller 65 has a circuit that includes a central processing unit (CPU) and a memory to operate with the CPU. Using signals sent from the light receiving device 61h, the controller 65 performs calculation and controls driving of the visible light source 62b, the infrared light source 61b, and the motors 62d and 61i. The controller 65 drives the measurement unit 61, simultaneously referring to the output from the measurement unit 61. In addition, the controller 65 drives the visible light source 62b, simultaneously controlling the motor 62d. In this way, the controller 65 controls positioning of the target 62a and the visible light source 62b, and performs scanning of the positions. Furthermore, the controller 65 outputs the information, which is related to an image of the examined eye 60 sent by the image capturing unit 59, to the monitor 70.

The controller 65 includes a refractive power measuring portion 66 and a level calculating portion 67. The refractive power measuring portion 66 measures a normal refractive power while controlling the measurement unit 61 and the projector 62. The level calculating portion 67 that is continuously operates during measurement calculates a tilt angle of the light receiving device 61h about the optical axis O of the instrument 51 for measuring a refractive power, with respect to the X-axis, outputting real time the tilt angle to the monitor 70. This allows an operator to recognize the tilt angle of the instrument 51.

Figure 4A:
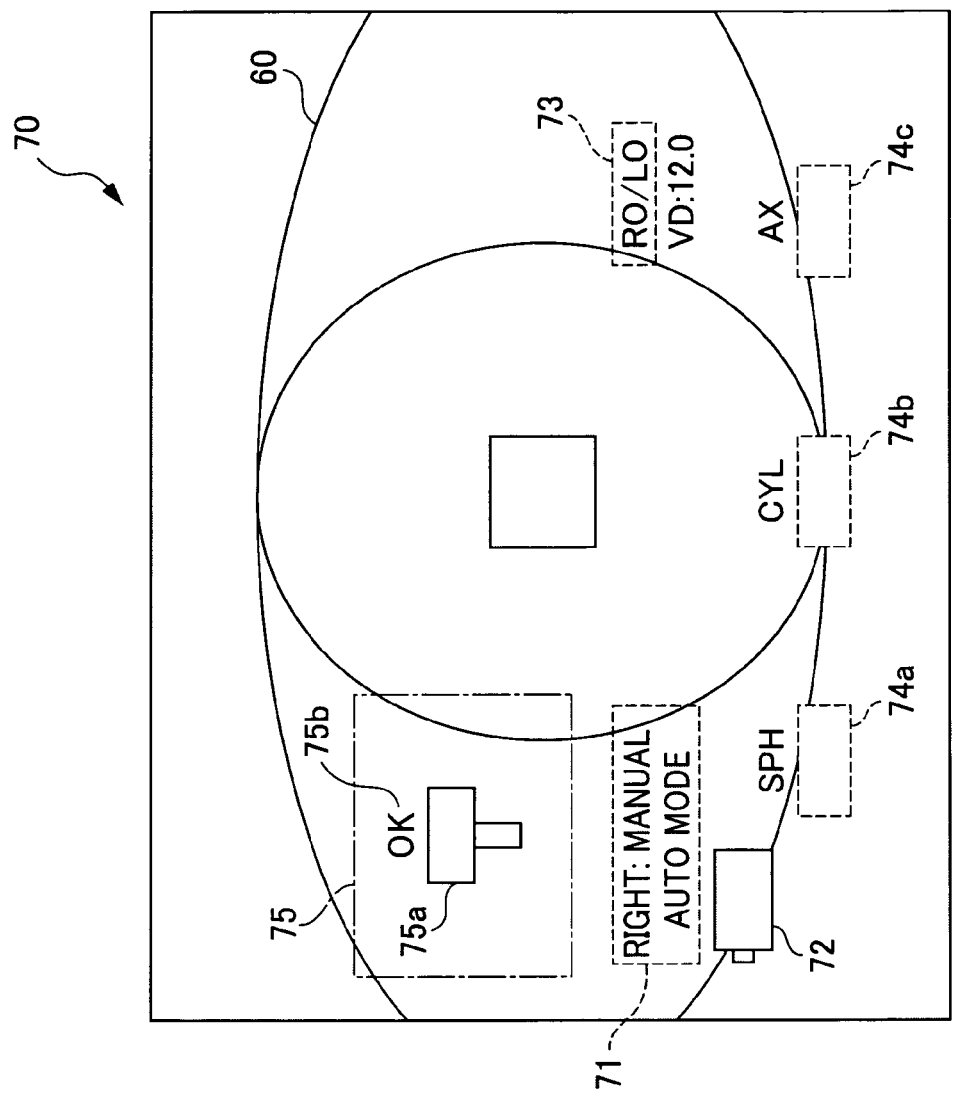
FIGS. 4A to 4C are schematic diagrams illustrating an example of display by a monitor according to the exemplary embodiment.

The monitor 70 is a display such as a Liquid Crystal Display (LCD) for performing a display of an image of the examined eye 60 captured by the image capturing unit 59 and various types of information related to image capturing. The monitor 70 is installed in a back portion of the instrument 51 for measuring a refractive power. An operator performs a measurement, checking the information displayed on the monitor 70. As shown in FIG. 4A, an displaying area of the monitor 70, in which an image of the examined eye 60 is displayed, includes a measurement mode area 71, a battery capacity area 72, a measurement number area 73, measured data areas 74a to 74c, and a tilt angle area 75. On the measurement mode area 71 and a measurement mode are displayed. On the battery capacity area 72 the capacity of a battery is displayed. The number of measurements for each of the left and right eyes of an examinee is displayed in the measurement number area 73. Measured data is displayed in the measured data area 74a to 74c, which includes data related to degrees of nearsightedness, farsightedness, astigmatism, and a tilt of an astigmatic axis. A tilt angle of the light receiving device 61h, which is equivalent to that of the instrument 51 for measuring a refractive power, is displayed in the tilt angle area 75.

The information related to the tilt angle of the instrument 51 that is calculated by the level calculating portion 67 based on the output from the horizontal sensor 64 is displayed (notified) in the tilt angle area 75. A conceptual diagram 75a illustrating the instrument 51 (as viewed in the X-axis direction) and an instruction of correction 75b indicating a correction required for the tilt angle are displayed in the tilt angle area 75.

FIG. 4A depicts a case where the tilt angle of the instrument 51 for measuring a refractive power is appropriate. In the tilt angle area 75, the conceptual diagram 75a illustrating the instrument 51 in an upright position and the instruction of correction 75b indicating "OK" are displayed.

Figure 4B:
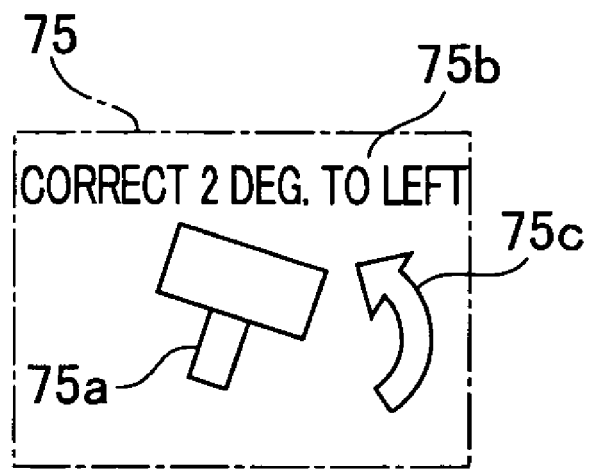

FIG. 4B depicts the instrument 51 rotated two degrees in a right direction about the X-axis. In the tilt angle area 75, the conceptual diagram 75a illustrating the instrument 51 in a rotated position and the instruction of correction 75b indicating "two degrees to the left" with an arrow 75c are displayed so as to instruct an operator to correct the instrument 51 into an upright position.

Figure 4C:
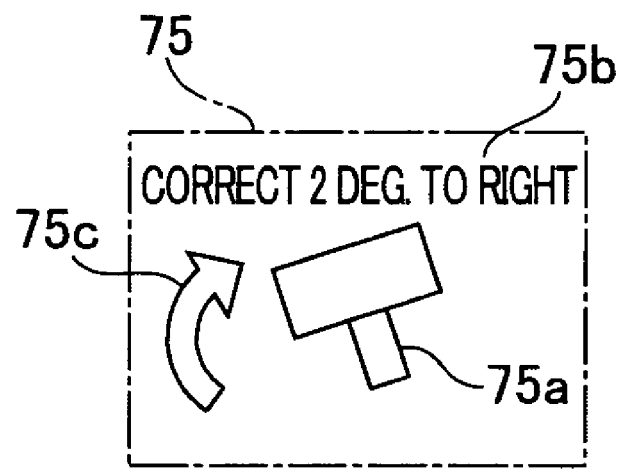

FIG. 4C depicts the instrument 51 rotated two degrees in a left direction about the X-direction, which is opposite to FIG. 4B.

It should be noted that it may be preferable, but not necessary, to display the instruction of correction approximately at two degrees (2, 4, 6 degrees . . . ) for convenience of an operator. The reason for this is that if it is displayed at one degree, for example, the display varies so frequently as to make the operator feel annoyed.

Operation of the Instrument

A description is given of the operation performed by the controller 65 in the instrument 51 for measuring a refractive power.

As described above, it is possible for the present embodiment to obtain data of one measurement (sampling data) with one rotation of the motor 61i (chopper 61a). Accordingly, the data obtained by this one rotation is called one set of samples. If the motor 61i rotates at 6000 rpm, it takes 0.01 sec to perform one rotation. Since it is hard to obtain stable data at such a high speed, the controller 65 performs a plurality of numbers of sampling so as to judge the stability (a difference between the maximum and the minimum values of sampling data, for example).

Correction of an Inclination Angle Based on Information from the Level Calculating Portion When an examinee undergoes a measurement, he orients his eye in an X-axis direction in a horizontal plane, while keeping an upright position. Accordingly, a line connecting substantially central points of left and right eyes is parallel with a Y-axis direction in the horizontal plane. The instrument 51 for measuring a refractive power is most appropriately positioned for a measurement as follows: Set the light for measurement to enter the examined eye 60 while the optical axis O of the light is adjusted to be aligned with the line of sight of the examined eye 60 (see FIG. 1). At the same time, set an axis $M_y$ for scanning to be parallel with the Y-axis in the horizontal plane (see FIG. 3).

When the light enters the examined eye 60 and the measurement starts, the level calculating portion 67 calculates a tilt angle of the light receiving device 61h about the X-axis based on the output from the horizontal sensor 64, outputting real time the tilt angle to the monitor 70.

As a result, the operator can recognize the tilt angle of the instrument 51, as described with FIGS. 4A to 4C. Accordingly, the operator can adjust the tilt angle according to information related to the tilt angle of the instrument 51 displayed on the monitor 70.

In this way, the instrument 51 is positioned such that the direction of the axis $M_y$ for scanning is parallel with the Y-axis in the horizontal plane and the direction of scanning is in agreement with the horizontal direction (Y-axis) and the vertical direction (Z-axis). The instrument 51 for measuring a refractive power can decrease the error of measured data due to the tilt angle, increasing the reliability of the measured data, particularly for an astigmatic axis.

In this connection, medical facilities such as ophthalmological clinics often face difficulty in using a desktop instrument for a measurement of an examinee, such as a low age person (baby or infant), or an examinee sitting in a wheelchair. This is due to the fact that the desktop instrument requires an examinee to keep a posture necessary for a measurement. Accordingly, such a handheld instrument as the one according to the present embodiment is widely used instead. However, a conventional handheld instrument for measuring a refractive power does not have high reliability for an astigmatic axis (axial angle of astigmatism) due to handshaking of an operator. In contrast, since the instrument 51 for measuring a refractive power allows an operator to easily correct a tilt angle of the instrument 51, it can increase the reliability of measured data.

As described above, the instrument 51 for measuring a refractive power that detects a tilt angle relative to the measurement reference and display it on the monitor 70 allows an operator to correct the tilt angle. Accordingly, the instrument 51 can increase the reliability of measured data, particularly an astigmatic axis.

While the invention has been described in detail and with reference to specific embodiments thereof, it will be apparent to one skilled in the art that various changes and modifications can be made therein without departing from the spirit and scope thereof. The description has been given of exemplary advantages, and the invention is not limited to these advantages. In addition, it is possible to combine the embodiment described above and modifications to be described later. A detail description of the combinations is omitted.

Modifications

Various modifications and changes may be adopted without departing from the spirit and scope of the present invention.

Although the description has been given of an example in which the reference line of a measurement is the axis in the horizontal plane, the present invention is not limited to this example. It may alternatively possible to adopt a line connecting substantially central points of left and light eyes of an examinee such that an operator corrects a tilt angle of an instrument for measuring a refractive power. In this case, it may be possible to employ an image sensor such as a CCD that can simultaneously capture images of both left and right eyes of the examinee and a controller that is configured to determine the line based on the captured images. In this way, an operator can obtain measured data with high reliability by correcting a tilt angle of an instrument for measuring a refractive power even if an examinee is not in an upright position. In addition, since this instrument does not need a detector such as an accelerometer, it is possible for the instrument to perform a measurement even if an examinee horizontally lies orienting his eyes vertically or horizontally.

Although the description has been given of an example in which the instrument obtains the measured data with high reliability by correcting the tilt angle of the instrument, the present invention is not limited to this example. It may alternatively be possible for the level calculating portion to store the measured tilt angle in a memory device so as to compensate the measured data of an astigmatic axis with the tilt angle. The compensation can be done in such a manner that the angle data obtained by the level calculating portion is added to the data of an astigmatic axis. In this way, even if there is a tilt angle mechanically uncorrected, the instrument can obtain the measurement data with high reliability by compensation.

Although the description has been given of an example in which the instrument for measuring a refractive power is of a handheld type, the present invention is not limited to this example. It may alternatively be possible that the instrument is of a desktop type. Even if a table on which the instrument is placed has an inherent tilt, it is possible to cancel the tilt by adjusting a tilt angle of the instrument, providing the measurement data with high reliability.

What is claimed is:

1. An instrument for measuring a refractive power including an astigmatic axis with retinoscopy, comprising:
   a projector for projecting light into a pupil of an examined eye;
   a light receiving device for receiving light reflected from the examined eye;
   a detector for detecting a tilt angle of the light receiving device with respect to a measurement reference; and
   a notification unit for conveying information related to a result of detection performed by the detector; wherein
   the notification unit comprises a monitor for displaying change in required orientation of said instrument an operator must make to correct the tilt angle, wherein
   the projector comprises a convex lens, a target and a visible light source arranged in this order away from an eye being examined, in addition to a motor, and
   said light receiving device additionally comprising an image capturing unit having a half mirror, convex lenses arranged on the opposite sides of the half mirror and a charge-coupled device, and
   a dichroic mirror arranged such that light coming from the examined eye is reflected off the dichroic minor, penetrates the half mirror and is guided to an image capturing surface of the charge-coupled device through the convex lenses, and
   rays of light from the target are illuminated by the visible light source and focused on a retina of the eye being examined after passing through the convex lens of the projector, reflecting off the half mirror, passing through one of the convex lenses of the image capturing unit, then reflecting off the dichroic mirror and entering the eye being examined.

2. The instrument according to claim 1, wherein the measurement reference is a reference line extending in one of horizontal and vertical directions.

3. The instrument according to claim 1, wherein the measurement reference is a reference line that connects substantially central points of left and right eyes of an examinee.

4. The instrument according to claim 1, further comprising a refractive power measuring portion that compensates data related to the measured astigmatic axis in accordance with the result of detection performed by the detector.

5. The instrument according to claim 1, wherein the instrument is of a handheld type to allow an operator to perform measurement while holding the instrument.

6. The instrument according to claim 1, wherein the detector includes an accelerometer.

7. The instrument according to claim 1, further comprising a level calculating portion, wherein the level calculating portion performs calculation of the tilt angle based on a signal sent from the detector.

8. The instrument according to claim 7, wherein the level calculating portion performs transmission of the resulting tilt angle to the monitor.

9. The instrument according to claim 8, wherein the monitor includes a display window that performs a display of the tilt angle.

10. The instrument according to claim 8, wherein the monitor displays instructions of correction in increments of double degrees.

11. The instrument according to claim 7, further comprising a refractive power measuring portion measuring a normal refractive power while controlling the projector and detector.

12. The instrument according to claim 1, wherein the target and visible light source are movable along an optical axis of the eye being examined with relative position between the target and visible light source maintained constant.

13. The instrument according to claim 1, wherein the dichroic mirror is positioned to allow infrared light coming from the examined eye to pass through and return to the light receiving device and reflect visible light coming from the examined eye towards the charge-coupled device.

14. An instrument for measuring a refractive power including an astigmatic axis with retinoscopy, comprising:
   a projector for projecting light into a pupil of an examined eye;
   a light receiving device for receiving light reflected from the examined eye;
   a detector for detecting a tilt angle of the light receiving device with respect to a measurement reference; and
   a notification unit for conveying information related to a result of detection performed by the detector; wherein
   the notification unit comprises a monitor for displaying change in required orientation of said instrument an operator must make to correct the tilt angle,
   wherein the light receiving device additionally comprises a chopper with slits, a motor for rotationally driving the chopper, an infrared light source for illuminating the chopper, lenses arranged on opposite sides of the chopper for projecting a pattern generated by the chopper onto the eye being examined, a light receiver arranged on a side of one of said lenses opposite said chopper, a half mirror also arranged on a side of this lens opposite said chopper, and a lens and an aperture diaphragm arranged in this order between said half mirror and light receiver, such that the pattern formed by returning light reflected off the eye being examined passes through the half mirror, lens and aperture diaphragm to said light receiver.

* * * * *